United States Patent
Chirik et al.

(10) Patent No.: US 9,394,325 B2
(45) Date of Patent: Jul. 19, 2016

(54) ENANTIOPURE BASE-METAL CATALYSTS FOR ASYMMETRIC CATALYSIS AND BIS(IMINO)PYRIDINE IRON ALKYL COMPLEXES FOR CATALYSIS

(75) Inventors: Paul J. Chirik, Princeton, NJ (US); Sebastien Monfette, Gatineau (CA); Jordan M. Hoyt, Palm Harbor, FL (US); Max R. Friedfeld, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 13/589,437

(22) Filed: Aug. 20, 2012

(65) Prior Publication Data
US 2013/0079567 A1 Mar. 28, 2013

Related U.S. Application Data

(60) Provisional application No. 61/525,404, filed on Aug. 19, 2011, provisional application No. 61/527,484, filed on Aug. 25, 2011, provisional application No. 61/604,345, filed on Feb. 28, 2012.

(51) Int. Cl.

| | |
|---|---|
| C07F 15/00 | (2006.01) |
| C07F 15/06 | (2006.01) |
| C07F 15/02 | (2006.01) |
| C07C 5/02 | (2006.01) |
| C07F 15/04 | (2006.01) |
| C07C 41/20 | (2006.01) |
| C07C 5/03 | (2006.01) |
| B01J 31/18 | (2006.01) |

(52) U.S. Cl.
CPC ............ *C07F 15/06* (2013.01); *B01J 31/182* (2013.01); *B01J 31/183* (2013.01); *B01J 31/184* (2013.01); *B01J 31/1815* (2013.01); *B01J 31/1835* (2013.01); *C07C 5/02* (2013.01); *C07C 5/03* (2013.01); *C07C 41/20* (2013.01); *C07F 15/02* (2013.01); *C07F 15/025* (2013.01); *C07F 15/04* (2013.01); *C07F 15/045* (2013.01); *C07F 15/065* (2013.01); *B01J 2231/645* (2013.01); *B01J 2531/0241* (2013.01); *B01J 2531/842* (2013.01); *B01J 2531/845* (2013.01); *C07B 2200/07* (2013.01); *C07C 2101/14* (2013.01); *C07C 2102/24* (2013.01); *C07C 2531/22* (2013.01); *Y02P 20/52* (2015.11)

(58) Field of Classification Search
None
See application file for complete search history.

(56) References Cited

U.S. PATENT DOCUMENTS

| 6,916,931 B2 | 7/2005 | Bianchini | |
|---|---|---|---|
| 6,927,313 B2 | 8/2005 | Bianchini | |
| 8,236,915 B2 * | 8/2012 | Delis et al. | 528/14 |
| 2011/0009573 A1 * | 1/2011 | Delis et al. | 525/453 |

FOREIGN PATENT DOCUMENTS

WO   WO 02/10133 A1 * 2/2002

OTHER PUBLICATIONS

Jones, DJ. et al. Novel supported Rh, Pt, Ir and Ru mesoporous aluminosilicates as catalysts for the hydrogenation of naphthalene. Applied Catalysis A: General. 2003, vol. 251, p. 132.*
Gilbertson, JD. et al. Synthesis and Stabilization of a Monomeric Iron(11) Hydroxo Complex via Intramolecular Hydrogen Bonding in the Secondary Coordination Sphere. Inorg. Chem. 2010, vol. 49, p. 8658.*
Carey, FA. Organic Chemistry 6th Ed. McGraw Hill. 2006, chapter 1, p. 9.*
Johnstone, RA. et al. Heterogeneous Catalytic Transfer Hydrogenation and Its Relation to Other Methods for Reduction of Organic Compounds. Chem. Rev. 1985, vol. 85, p. 141.*
Dorwold, FZ. Side Reactions in Organic Synthesis. Wiley. 2005, preface.*
Bianchini, C. et al. Simultaneous Polymerization and Schulz-Flory Oligomerization of Ethylene Made Possible by Activation with MAO of a C1-Symmetric [2,6-Bis(arylimino)pyridyl]iron Dichloride Precursor. Organometallics. 2004, vol. 23, p. 6089.*
Budzelaar, PHM. et al. Olefin hydrogenation using diimine pyridine complexes of Co and Rh. Journal of Molecular Catalysis A: Chemical. 2005, vol. 232, p. 151.*
Jenkins, DM. et al. Elucidation of a Low Spin Cobalt(II) System in a Distorted Tetrahedral Geometry. JACS. 2002, vol. 124, p. 15336.*
C. Bianchini et al. "Oligomerisation of Ethylene to Linear α-Olefins by new $C_S$- and $C_1$-Symmetric[2,6-Bis(imino)pyridyl]iron and -cobalt Dichloride Complexes," European Journal of Inorganic Chemistry, 2003, 1620-1631.
M. W. Bouwkamp et al. "Bis(imino)pyridine Iron (II) Alkyl Cations for Olefin Polymerization," Journal of the American Chemical Society, 2005, 127, 9660-9661.
M. W. Bouwkamp et al. "Square planar bis(imino)pyridine iron halide and alkyl complexes," Chemical Communications. 2005, 3406-3408.
I. Fernandez et al. "Synthesis of Bis(imino)pyridine Iron Di- and Monoalkyl Complexes: Stability Differences between $FeCH_2SiMe_3$ and $FeCH_2CMe_3$ Derivatives," Organometallics, 2008, 27, 109-118.

(Continued)

*Primary Examiner* — Rita Desai
*Assistant Examiner* — Ben S Michelson
(74) *Attorney, Agent, or Firm* — Oblon, McClelland, Maier & Neustadt, L.L.P.

(57) ABSTRACT

A transition metal-containing compound having a tridentate chiral ligand bound to iron, cobalt, or nickel. The tridentate ligands are bound to the metal via nitrogen, phosphorus, and/or arsenic atoms. The tridentate ligand has a chiral group bound at least one of the nitrogen, phosphorus, and arsenic atoms, and a blocking group may be bound to another one of the nitrogen, phosphorus, and arsenic atoms. The transition metal-containing compound is useful for the catalyzing the asymmetric hydrogenation of olefins.

30 Claims, No Drawings

(56) References Cited

OTHER PUBLICATIONS

R. Trovich et al. "Bis(imino)pyridine Iron Alkyls Containing β-Hydrogens: Synthesis, Evaluation of Kinetic Stability, and Decomposition Pathways Involving Chelate Participation," Journal of the American Chemical Society, 2008, 130, 11631-11640.

Q. Knijnenburg et al. "Olefin hydrogenation using diamine pyridine complexes of Co and Rh," Journal of Molecular Catalysis A: Chemical, 232, 2005, 151-159.

M. Humphries et al. "Investigations into the Mechanism of Activation and Initiation of Ethylene Polymerization by Bis(imino)pyridine Cobalt Catalysts: Synthesis, Structures, and Deuterium Labeling Studies," Organometallics, 2005, 24, 2039-2050.

V. Gibson et al. "Bis(imino)pyridine cobalt alkyl complexes and their reactivity towards ethylene: a model system for β-hydrogen chain transfer," Chemical Communications, 2002, 2316-2317.

K. Tellmann et al. "Experimental and Computational Study of β-H Transfer between Cobalt(I) Alkyl Complexes and 1-Alkenes," Organometallics, 2004, 23. 5503-5513.

D. Zhu et al. "$(Py)_2Co(CH_2SiMe_3)_2$ As an Easily Accessible Source of $CoR_2$," Organometallics, 2010, 29, 1897-1908.

K. Sylvester et al. "Iron-Catalyzed, Hydrogen-Mediated Reductive Cyclization of 1,6-Enynes and Diynes: Evidence for Bis(imino)pyridine Ligand Participation," 2009, 131, 8772-8774.

* cited by examiner

ENANTIOPURE BASE-METAL CATALYSTS FOR ASYMMETRIC CATALYSIS AND BIS(IMINO)PYRIDINE IRON ALKYL COMPLEXES FOR CATALYSIS

CROSS REFERENCE TO RELATED APPLICATIONS

The present application claims the benefit of U.S. Provisional Application No. 61/525,404, filed on Aug. 19, 2011, U.S. Provisional Application No. 61/527,484 filed on Aug. 25, 2011, and U.S. Provisional Application No. 61/604,345, filed on Feb. 28, 2012, which are herein incorporated by reference in their entireties.

STATEMENT REGARDING FEDERALLY SPONSORED RESEARCH OR DEVELOPMENT

A part of this invention was made with government support under Grant CHE 1026084 awarded by the National Science Foundation. The government has certain rights in this invention.

FIELD OF THE INVENTION

This invention relates to transition metal-containing compounds, more specifically to iron, cobalt, or nickel complexes having tridentate chiral ligands, and to methods of making these transition metal-containing compounds. The compounds of the present invention are effective in catalyzing the asymmetric hydrogenation of olefins. The invention also relates to methods of hydrogenating and transforming olefins and alkynes with iron-containing compounds having tridentate achiral ligands.

BACKGROUND OF THE INVENTION

Asymmetric hydrogenation of olefins, a Nobel Prize winning reaction, is now ubiquitous in both research and industrial laboratories. Present technologies rely upon precious metal catalysts (Rh, Ir, Ru, Pd, Pt, etc.) in conjunction with chiral phosphine ligands to accomplish the asymmetric hydrogenation of olefins. These metals and ligands are expensive when compared to base metals such as iron. Thus, there is an incredible cost incentive to use base-metal catalysts, which can be orders of magnitude less expensive than their precious metal counterparts. The precious metals and the phosphine ligands are also toxic. Additional measures must therefore be taken to remove the catalyst system from the hydrogenated products following hydrogenation.

Aryl-substituted bis(imino)pyridine iron and cobalt compounds have emerged as an effective class of base metal olefin hydrogenation catalysts. Each of Bouwkamp, M. W. et al. (*J. Am. Chem. Soc.* 2005, 127, 9660-9661), Bouwkamp, M. W. et al. (*Chem. Commun.* 2005, 3406-3408), Fernández, I. et al. (*Organometallics* 2008, 27, 109-118), and Trovitch, R. J. et al. (*J. Am. Chem. Soc.* 2008, 130, 11631-11640) discloses four or five coordinate iron compounds that have $\kappa^3$-bis(imino)pyridyl ligands bound thereto. In each case, the $\kappa^3$-bis(imino)pyridyl ligands were achiral or symmetric and achiral. Some of these iron compounds were shown to catalyze olefin polymerizations, but there is no disclosure in any of these references of hydrogenating or transforming olefins (preferably prochiral) and alkynes. There is also no disclosure that these compounds would be useful for such reactions.

Cobalt compounds having $\kappa^3$-bis(imino)pyridyl ligands are also known in the art. Each of Knijnenburg, Q. et al. (*J. Mol. Catal. A* 2005, 232, 151-159), Humphries, M. J. et al. (*Organometallics* 2005, 24, 2039-2050), Gibson, V. C. et al. (*Chem. Commun.* 2002, 2316-2317), Tellmann, K. P. et al. (*Organometallics* 2004, 23, 5503-5513), and Zhu et al. (*Organometallics* 2010, 29, 1897-1908) discloses four or five coordinate cobalt compounds that have $\kappa^3$-bis(imino)pyridyl ligands bound thereto. The $\kappa^3$-bis(imino)pyridyl ligands in these disclosures are symmetric and achiral, and the compounds having these ligands were shown to be useful for polymerization and hydrogenation of α-olefins. However, these references also fail to disclose hydrogenating or transforming further substituted olefins (preferably prochiral) and alkynes or that such compounds would be useful for these reactions. Accordingly, modified ligand architectures are required to generate single enantiomer catalysts for asymmetric olefin hydrogenation and for transformation of olefins and alkynes.

Bianchini et al. (*Eur. J. Inorg. Chem.* 2003, 1620-1631) discloses a modified ligand architecture, which is a $C_1$ symmetric $\kappa^3$-bis(imino)pyridyl ligand where the nitrogen atom of one imine moiety has a large 2,6-diisopropyl aryl ring bonded thereto and the nitrogen atom of the other imine moiety has a chiral group. These ligands were bound to cobalt and iron dihalide sources to form five coordinate dihalide compounds, which were shown to be useful, when combined with methylaluminoxane (MAO), for ethylene polymerization. Bianchini and coworkers have also disclosed transition metal compounds having $\kappa^3$-thiophenyl(imino)pyridyl ligands, and the use of these compounds for the polymerization/oligomerization of ethylene/α-olefins in U.S. Pat. Nos. 6,927,313 and 6,916,931. However, there is no disclosure in these references of hydrogenating prochiral olefins in the presence of these transition metal compounds, nor is there any disclosure that the compounds disclosed therein would be efficient for this reaction.

In view of the foregoing, there is a need for compounds comprised of first row transition metals and ligands operable for the hydrogenation of olefins, preferably prochiral olefins, and/or the transformation of alkynes. The present inventors have provided a solution to this problem with the invention disclosed herein.

BRIEF SUMMARY OF THE INVENTION

One object of the present invention is to provide transition metal-containing compounds having tridentate ligands, where the transition metal is iron, nickel, or cobalt and the tridentate ligands have at least one chiral moiety. Another object of the invention is to provide methods of making the transition metal-containing compounds of the present invention. A further object of the invention is to provide catalysts that comprise the transition metal-containing compounds of the invention, and methods of using these catalysts to catalyze the asymmetric hydrogenation of olefins.

These and other objects of the invention are, individually or combined accomplished with transition metal-containing compounds represented by formula (I):

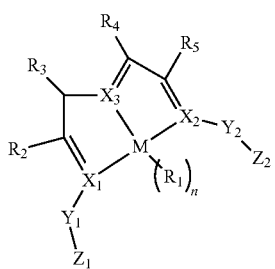

(I)

or salts thereof,
wherein
M represents a transition metal atom selected from the group consisting of iron, cobalt, and nickel;
each of $X_1$, $X_2$, and $X_3$, individually, represents an element selected from the group consisting of nitrogen, phosphorus, and arsenic;
$Y_1$ represents a chemical bond between $X_1$ and $Z_1$ or a carbon-containing group that links $X_1$ and $Z_1$;
$Y_2$ represents a chemical bond between $X_2$ and $Z_2$ or a carbon-containing group that links $X_2$ and $Z_2$;
each of $Z_1$ and $Z_2$ represents a chiral group represented by formula (II) or a blocking group, with the proviso that at least one of $Z_1$ and $Z_2$ represents a chiral group represented by formula (II):

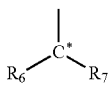

(II)

wherein each of $R_6$ and $R_7$, individually, represents $C_{1-20}$ alkyl group optionally having at least one heteroatom, a $C_{3-20}$ (hetero)cycloalkyl group, a $C_{5-30}$(hetero)aryl group, with the proviso that $R_6$ and $R_7$ do not simultaneously represent the same group, C* represents a nonracemic chiral carbon atom, and C* is bound to the $Y_1$ or $Y_2$ group or bound to $X_1$ or $X_2$ when $Y_1$ or $Y_2$ represents a chemical bond;
n represents an integer of 1 or 2;
each $R_1$, individually, represents a chemical bond to a carbon atom of $Y_1$, $Y_2$, $Z_1$ or $Z_2$, a hydrogen atom, a $C_{1-20}$ alkyl group optionally having at least one heteroatom, a $C_{3-20}$ (hetero)cycloalkyl group, a $C_{5-30}$(hetero)aryl group, or a halogen atom, with the proviso that when n represents an integer of 2, each $R_1$ does not, simultaneously, represent a halogen atom;
each of $R_2$ to $R_5$, individually, represents a $C_{1-20}$ alkyl group optionally having at least one heteroatom, a $C_{3-20}$ (hetero)cycloalkyl group, and an $C_{5-30}$(hetero)aryl group;
$R_2$ and $R_3$, together, can form a saturated, an unsaturated, or an aromatic ring having four, five, or six carbon atoms that is optionally interrupted with a heteroatom and is optionally substituted;
$R_3$ and $R_4$, together, can form a saturated, an unsaturated, or an aromatic ring having four, five, or six carbon atoms that is optionally interrupted with a heteroatom and is optionally substituted;
$R_4$ and $R_5$, together, can form a saturated, an unsaturated, or an aromatic ring having four, five, or six carbon atoms that is optionally interrupted with a heteroatom and is optionally substituted;
$R_2$ can form a saturated, an unsaturated, or an aromatic ring with a carbon atom of $Y_1$ or a carbon atom of $Z_1$, the saturated, an unsaturated, or an aromatic ring having four, five, or six carbon atoms, is optionally interrupted with a heteroatom, and is optionally substituted; and
$R_5$ can form a saturated, an unsaturated, or an aromatic ring with a carbon atom of $Y_2$ or a carbon atom of $Z_2$, the saturated, an unsaturated, or an aromatic ring having four, five, or six carbon atoms, is optionally interrupted with a heteroatom, and is optionally substituted.

Another object of the present invention is to provide methods of hydrogenating or transforming olefins and alkynes with iron-containing compounds. This object is accomplished by methods comprising reacting hydrogen with an olefin, an alkyne, or a mixture thereof, in the presence of at least one iron-containing compound represented by formula (III):

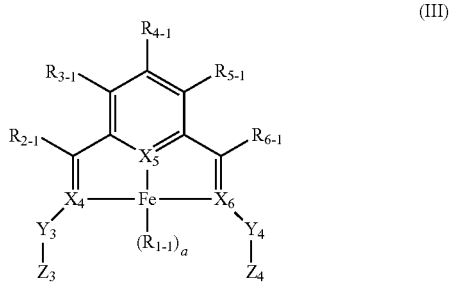

(III)

or a salt thereof,
wherein
each of $X_4$, $X_5$, and $X_6$, individually, represents an element selected from the group consisting of nitrogen, phosphorus, and arsenic;
$Y_3$ represents a chemical bond between $X_4$ and $Z_3$ or a carbon-containing group that links $X_4$ and $Z_3$;
$Y_4$ represents a chemical bond between $X_6$ and $Z_4$ or a carbon-containing group that links $X_6$ and $Z_4$;
each of $Z_3$ and $Z_4$, individually, represents a blocking group or a chiral group represented by formula (II);
a represents an integer of 1 or 2;
$R_{1-1}$, represents a chemical bond to a carbon atom of $Y_3$, $Y_4$, $Z_3$ or $Z_4$, a hydrogen atom, a $C_{1-20}$ alkyl group optionally having at least one heteroatom, a $C_{3-20}$ (hetero)cycloalkyl group, or a $C_{5-30}$(hetero)aryl group;
each of $R_{2-1}$ to $R_{6-1}$, individually, represents a hydrogen atom, a $C_{1-20}$ alkyl group optionally having at least one heteroatom, a $C_{3-20}$ (hetero)cycloalkyl group, or a $C_{5-30}$ (hetero)aryl group;
$R_{2-1}$ can form a (hetero)ring with a carbon atom from $Y_3$ or $Z_3$;
$R_{6-1}$ can form a (hetero)ring with a carbon atom from $Y_4$ or $Z_4$;
$R_{2-1}$ and $R_{3-1}$, together, can form a saturated, an unsaturated, or an aromatic ring having four, five, or six carbon atoms, is optionally interrupted with a heteroatom, and is optionally substituted; and
$R_{5-1}$ and $R_{6-1}$, together, can form a saturated, an unsaturated, or an aromatic ring having four, five, or six carbon atoms, is optionally interrupted with a heteroatom, and is optionally substituted.

DETAILED DESCRIPTION OF THE INVENTION

The present inventors have synthesized transition metal-containing compounds comprised of tridentate ligands having at least one chiral moiety and first row transition metal atoms such as iron, nickel, and cobalt. The present inventors have found that these transition metal-containing compounds are highly active in the hydrogenation of olefins, particularly prochiral olefins, that prove challenging for current catalysts. The present inventors have also synthesized iron-containing compounds comprised of achiral tridentate ligands and an alkyl group that are useful for the hydrogenation and transformation of olefins and alkynes. Further, the modularity of the present invention is an incredibly attractive aspect allowing catalyst evaluation by high throughput screening. This is beneficial when considering novel and difficult substrates for asymmetric olefin hydrogenation. A variety of ligands can be quickly screened to find the system with the best activity.

The transition metal-containing compounds of the present invention are represented by formula (I):

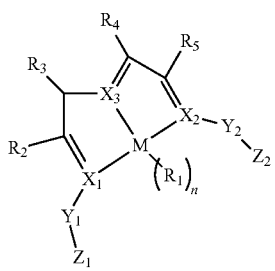

(I)

wherein

M represents a transition metal atom selected from the group consisting of iron, cobalt, and nickel;

each of $X_1$, $X_2$, and $X_3$, individually, represents an element selected from the group consisting of nitrogen, phosphorus, and arsenic;

$Y_1$ represents a chemical bond between $X_1$ and $Z_1$ or a carbon-containing group that links $X_1$ and $Z_1$;

$Y_2$ represents a chemical bond between $X_2$ and $Z_2$ or a carbon-containing group that links $X_2$ and $Z_2$;

each of $Z_1$ and $Z_2$ represents a chiral group represented by formula (II) or a blocking group, with the proviso that at least one of $Z_1$ and $Z_2$ represents a chiral group represented by formula (II):

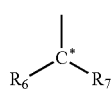

(II)

wherein each of $R_6$ and $R_7$, individually, represents $C_{1-20}$ alkyl group optionally having at least one heteroatom, a $C_{3-20}$ (hetero)cycloalkyl group, a $C_{5-30}$(hetero)aryl group, with the proviso that $R_6$ and $R_7$ do not simultaneously represent the same group, C* represents a nonracemic chiral carbon atom, and C* is bound to the $Y_1$ or $Y_2$ group or bound to $X_1$ or $X_2$ when $Y_1$ or $Y_2$ represents a chemical bond;

n represents an integer of 1 or 2;

each $R_1$, individually, represents a chemical bond to a carbon atom of $Y_1$, $Y_2$, $Z_1$ or $Z_2$, a hydrogen atom, a $C_{1-20}$ alkyl group optionally having at least one heteroatom, a $C_{3-20}$ (hetero)cycloalkyl group, a $C_{5-30}$(hetero)aryl group, or a halogen atom, with the proviso that when n represents an integer of 2, each $R_1$ does not, simultaneously, represent a halogen atom;

each of $R_2$ to $R_5$, individually, represents a $C_{1-20}$ alkyl group optionally having at least one heteroatom, a $C_{3-20}$ (hetero)cycloalkyl group, and an $C_{5-30}$(hetero)aryl group;

$R_2$ and $R_3$, together, can form a saturated, an unsaturated, or an aromatic ring having four, five, or six carbon atoms that is optionally interrupted with a heteroatom and is optionally substituted;

$R_3$ and $R_4$, together, can form a saturated, an unsaturated, or an aromatic ring having four, five, or six carbon atoms that is optionally interrupted with a heteroatom and is optionally substituted;

$R_4$ and $R_5$, together, can form a saturated, an unsaturated, or an aromatic ring having four, five, or six carbon atoms that is optionally interrupted with a heteroatom and is optionally substituted;

$R_2$ can form a saturated, an unsaturated, or an aromatic ring with a carbon atom of $Y_1$ or a carbon atom of $Z_1$, the saturated, an unsaturated, or an aromatic ring having four, five, or six carbon atoms, is optionally interrupted with a heteroatom, and is optionally substituted; and $R_5$ can form a saturated, an unsaturated, or an aromatic ring with a carbon atom of $Y_2$ or a carbon atom of $Z_2$, the saturated, an unsaturated, or an aromatic ring having four, five, or six carbon atoms, is optionally interrupted with a heteroatom, and is optionally substituted.

The transition metal-containing compounds represented by formula (I) can be in the form of a salt.

As used herein, "$C_{1-20}$ alkyl group" includes straight and branched alkyl groups that have from one to twenty carbon atoms. Non-limiting examples of these groups include, but are not limited to, methyl, ethyl, propyl, and isobutyl groups.

As used herein, "$C_{3-20}$ (hetero)cycloalkyl group" includes cyclic alkyl groups that have from five to twenty carbon atoms. At least one heteroatom can be present in the ring structure of the cyclic alkyl hydrocarbon. Non-limiting examples of these groups include, but are not limited to, cyclopropyl, cyclobutyl, cyclopentyl, and cyclohexane groups.

As used herein, "$C_{5-30}$(hetero)aryl group" includes aryl groups that have from five to thirty carbon atoms. At least one heteroatom can be present in the ring structure of the aromatic hydrocarbon. The (hetero)aryl groups have at least one aromatic ring. Additional rings can be present in the (hetero)aryl groups, which may be fused or connected together by single bonds to the other aryl rings. Non-limiting examples of these groups include, but are not limited to, tolyl, xylyl, phenyl, and naphthyl groups.

Each of these groups are optionally substituted, where one hydrogen atom from the $C_{1-20}$ alkyl, $C_{3-20}$(hetero)cycloalkyl, or $C_{5-30}$(hetero)aryl group is removed and is replaced with a functional group. If not otherwise stated, the functional groups for these substituents contain 0 to about 30 carbon atoms, specifically from 0 to 20 carbon atoms, more specifically from 0 to 10 carbon atoms. The integers between these values are included, i.e. 1, 2, 3, 4, 5, 6, 7, 8, 9, 10, 11, 12, 13, 14, 15, 16, 17, 18, 19, 20, 21, 22, 23, 24, 25, 26, 27, 28, and 29. These functional groups are preferably non-protic groups, such as a tertiary amine group, a tertiary amide group, an ether group, and an ester group. The nitrogen atom of the amine/amide groups and the oxygen atom of the ether/ester groups can be replaced with another atom from Groups 15 and 16 of the periodic table of elements, respectively. The substituent groups do not substantially interfere with the hydrogenation processes described herein.

As used herein, "heteroatom" includes any of the Group 13-17 elements except carbon, and comprise, for example, an atom selected from the group consisting of oxygen, nitrogen, silicon, sulfur, phosphorus, fluorine, chlorine, bromine, and iodine.

As used herein, "halogen" includes any of the Group 17 elements. This group includes fluorine, chlorine, bromine, iodine and astatine. Preferably, the halogen is fluorine, chlorine, or bromine. The anions of these halogens are also included in this group. Accordingly and alternatively, preferred halogens are fluoride, chloride, and bromide. Without wishing to be bound to a particular theory, it is believed that the halogens are in the form of the halide when bound as a ligand to the transition metals disclosed herein.

As used herein, "olefin" includes organic compounds having at least one carbon-carbon double bond and "alkyne" includes organic compounds having at least one carbon-carbon triple bond. The alkynes can include, in addition to the at least one carbon-carbon triple bond, at least one carbon-carbon double bond.

Methyl groups are shown in the representations of transition metal-containing compounds included herein as "$CH_3$" or "Me". Ethyl groups, isopropyl groups, tert-butyl, cyclohexyl, and phenyl groups are shown in the representations of transition metal-containing compounds included herein as "Et," "iPr," "tBu," "Cy," and "Ph," respectively. Last, neosilyl groups are represented by "Ns" or "$CH_2TMS$."

In the transition metal-containing compounds represented by formula (I), M represents a transition metal atom selected from the group consisting of iron, cobalt, and nickel. In preferred embodiments, M represents a cobalt or an iron atom. In particularly preferred embodiments, M represents a cobalt atom.

In the transition metal-containing compounds represented by formula (I), each of $X_1$, $X_2$, and $X_3$, individually, represents an element selected from the group consisting of nitrogen, phosphorus, and arsenic. In preferred embodiments, at least one of $X_1$, $X_2$ and $X_3$ represents a nitrogen atom. In further preferred embodiments, at least two of $X_1$, $X_2$ and $X_3$ represent a nitrogen atom. In the most preferred embodiments, all three of $X_1$, $X_2$ and $X_3$ represent a nitrogen atom.

In the transition metal-containing compounds represented by formula (I), $Y_1$ represents a chemical bond between $X_1$ and $Z_1$ or a carbon-containing group that links $X_1$ and $Z_1$. The carbon-containing group is one that links or joins $X_1$ and $Z_1$ and has a chemical bond between each of $X_1$ and $Z_1$. This group is not particularly limited, so long as it does not remove the $Z_1$ group from the ligand sphere of the transition metal-containing compounds of the present invention, which could minimize the effect of the $Z_1$ group on the catalytic reactions. In preferred embodiments, $Y_1$ represents an alkylene group of one to six carbon atoms, which is represented by —$(CH_2)_m$—, where the symbol "-", in each occurrence, represents the chemical bond to each of $X_1$ and $Z_1$ and m is an integer of 1, 2, 3, 4, 5, or 6. The alkylene group can be substituted with at least one substituting group defined above. Preferably, the alkylene group is unsubstituted.

In the transition metal-containing compounds represented by formula (I), $Y_2$ represents a chemical bond between $X_2$ and $Z_2$ or a carbon-containing group that links $X_2$ and $Z_2$. The carbon-containing group is one that links or joins $X_2$ and $Z_2$ and has a chemical bond between each of $X_2$ and $Z_2$. This group is not particularly limited, so long as it does not remove the $Z_2$ group from the ligand sphere of the transition metal-containing compounds of the present invention, which could minimize the effect of the $Z_2$ group on the catalytic reactions. In preferred embodiments, $Y_2$ represents an alkylene group of one to six carbon atoms, which is represented by —$(CH_2)_m$—, where the symbol "-", in each occurrence, represents the chemical bond to each of $X_2$ and $Z_2$ and m is an integer of 1, 2, 3, 4, 5, or 6. The alkylene group can be substituted with at least one substituting group defined above. Preferably, the alkylene group is unsubstituted.

In the transition metal-containing compounds of the present invention, each of $Z_1$ and $Z_2$ represents a chiral group represented by formula (II) or a blocking group, with the proviso that at least one of $Z_1$ and $Z_2$ represents a chiral group represented by formula (II):

(II)

Each of $R_6$ and $R_7$, individually, represents a $C_{1-20}$ alkyl group optionally having at least one heteroatom, a $C_{3-20}$ (hetero)cycloalkyl group, a $C_{5-30}$(hetero)aryl group, provided that $R_6$ and $R_7$ do not simultaneously represent the same group. Non-limiting and preferred groups for each of $R_6$ and $R_7$ include a methyl group, an ethyl group, an isopropyl group, and a tert-butyl group. C* represents a nonracemic chiral carbon atom, and C* is bound to the $Y_1$ and/or $Y_2$ group or bound to $X_1$ and/or $X_2$ when $Y_1$ and/or $Y_2$ represents a chemical bond. In some embodiments, one of $Z_1$ and $Z_2$ represents a chiral group represented by formula (II) and the other of $Z_1$ and $Z_2$ represents a blocking group. In other embodiments, both $Z_1$ and $Z_2$ represent a chiral group represented by formula (II). As used herein, the term "nonracemic chiral carbon atom" relates to a predominance of one enantiomer over another, preferably at least 70:30 of the R or S enantiomer to the S or R enantiomer; more preferably at least 80:20 of the R or S enantiomer to the S or R enantiomer; and even more preferably at least 90:10 of the R or S enantiomer to the S or R enantiomer. In the most preferred embodiments, the group having the nonracemic chiral carbon atom is only in the form of the R or the S enantiomer.

Non-limiting examples of the blocking group include an isopropyl group; a tert-butyl group; a neopentyl group; a cyclopropyl group; a cyclobutyl group; a cyclopentyl group; a cyclohexyl group optionally substituted with at least one methyl group, at least one ethyl group, at least one isopropyl group, at least one tert-butyl group, or a combination thereof; a phenyl group optionally substituted with at least one methyl group, at least one ethyl group, at least one isopropyl group, at least one a tert-butyl group, or a combination thereof; an adamantyl group; a trimethylsilyl group; a triethylsilyl group; a tripropylsilyl group; a tri-iso-propyl silyl group; a tri-tert-butyl group; and a neosilyl group.

In other preferred embodiments, the blocking group is a group represented by formula (IV)

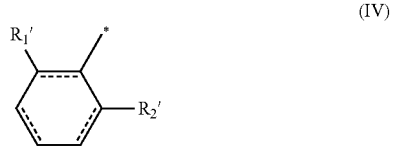

(IV)

where—* represents a chemical bond to $X_1$ or $X_2$, and each of $R_1'$ and $R_2'$ represents a hydrogen atom, a $C_{1-20}$ alkyl group optionally having at least one heteroatom, a $C_{3-20}$ (hetero)

cycloalkyl group, or a $C_{5-20}$ (hetero)aryl group; and each dashed bond, - - - -, represents an optional double bond. In preferred embodiments, each of $R_1'$ and $R_2'$ represents an isopropyl group or a tert-butyl group and each of the optional double bonds are present to form a phenyl ring. In particularly preferred embodiments, each of $R_1'$ and $R_2'$ represents an isopropyl group and each of the optional double bonds are present to form a phenyl ring.

In the transition metal-containing compounds represented by formula (I), n represents an integer of 1 or 2. When n represents 1, there is one $R_1$ group present in the transition metal-containing compounds represented by formula (I), and when n represents 2, there are two $R_1$ groups. Each $R_1$, individually, represents a chemical bond to a carbon atom of $Y_1$, $Y_2$, $Z_1$ and/or $Z_2$, a hydrogen atom, a $C_{1-20}$ alkyl group optionally having at least one heteroatom, a $C_{3-20}$ (hetero)cycloalkyl group, a $C_{5-30}$(hetero)aryl group, or a halogen atom, with the proviso that when n represents an integer of 2, each $R_1$ does not, simultaneously, represent a halogen atom. In preferred embodiments, n represents 1 and $R_1$ is a halide such as chloride. In other preferred embodiments, n represents 1 and $R_1$ represents an alkyl group such as a methyl group, an ethyl group, or a propyl group. In the most preferred embodiments, n represents 1 and $R_1$ represents a methyl group or a bond to a carbon atom of one of $Z_1$ and $Z_2$.

Some cyclometallated compounds are included within the scope of the present invention. In general, cyclometallated compounds are structurally similar to, for example, heterocycloalkanes, but where one carbon atom within the ring is replaced with a transition metal and the ring has at least one heteroatom, such as a nitrogen atom. Cyclometallated compounds are formed in the present invention by forming a chemical bond between the metal center M and, e.g., a carbon atom in the $Y_1$ and/or $Y_2$ group or a carbon atom in the $Z_1$ and/or $Z_2$ group. In the case of cyclometallated compounds, at least one of the $R_1$ group represents the chemical bond between the metal center M and the carbon atom of the $Y_1$, $Y_2$, $Z_1$, and/or $Z_2$ group.

In the transition metal-containing compounds represented by formula (I), each of $R_2$ to $R_5$, individually, represents a $C_{1-20}$ alkyl group optionally having at least one heteroatom, a $C_{3-20}$ (hetero)cycloalkyl group, and an $C_{5-30}$(hetero)aryl group. These groups are the same as those defined above. The couple of $R_2$ and $R_3$ and the couple of $R_4$ and $R_5$ can each, individually, be joined to form a ring having four, five or six carbon atoms that is optionally interrupted with a heteroatom. These rings can also, optionally, be substituted with a substituting group defined above. Preferably, each of $R_2$ and $R_5$ represents a methyl group, an ethyl group, an n-propyl group or an isopropyl group. More preferably, each of $R_2$ and $R_5$ represents a methyl group. In other preferred embodiments, $R_3$ and $R_4$, together, form a saturated, an unsaturated, or an aromatic ring having four, five, or six carbon atoms that is optionally interrupted with a heteroatom and is optionally substituted. In preferred embodiments, $R_3$ and $R_4$ are bonded together to form an aromatic ring such as a pyridine ring. In particularly preferred embodiments each of $R_2$ and $R_5$ represents a methyl group and $R_3$ and $R_4$ are joined together to form a pyridine ring.

In the transition metal-containing compounds represented by formula (I), $R_2$ can form a saturated, an unsaturated, or an aromatic ring with a carbon atom of $Y_1$ or a carbon atom of $Z_1$ that has four, five, or six carbon atoms, is optionally interrupted with a heteroatom, and is optionally substituted. Likewise, $R_5$ can form a saturated, an unsaturated, or an aromatic ring with a carbon atom of $Y_2$ or a carbon atom of $Z_2$ that has four, five, or six carbon atoms, is optionally interrupted with a heteroatom, and is optionally substituted. In preferred embodiments, each of $Y_1$ and $Y_2$ represents a methylene group and heterocycloalkyl rings are formed between each methylene carbon atom of $Y_1$ and $Y_2$ and $R_2$ and $R_5$.

The chiral ligands of the present invention are represented by

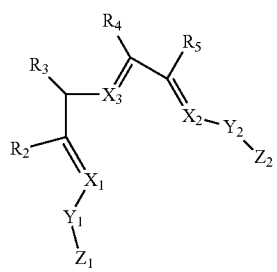

The ligands are bound to metal center M through each of $X_1$, $X_2$, and $X_3$, and therefore these ligands are tridentate ligands. The ligands herein are referred to as "$X^3$ ligands." Each of $X_1$, $X_2$, and $X_3$, individually, represents a nitrogen, phosphorus, or arsenic atom. In preferred embodiments, at least one of $X_1$, $X_2$ and $X_3$ represents a nitrogen atom. In further preferred embodiments, at least two of $X_1$, $X_2$ and $X_3$ represent a nitrogen atom. In the most preferred embodiments, all three of $X_1$, $X_2$ and $X_3$ represent a nitrogen atom. The synthesis of the $X^3$ ligands is known, and can be found in, for example, Bianchini et al. (*Eur. J. Inorg. Chem.* 2003, 1620-1631) and Monfette, S.; Turner, Z. R.; Semproni, S. P.; Chink, P. J. *J. Am. Chem. Soc.* 2012, 134(10), 4561-4564 (and the Supporting Information thereof).

Without wishing to be bound to a particular theory, it is believed that the tridentate ligands are likely bound to metal center M (e.g. iron, nickel, or cobalt) through dative bonds between metal center M and each of $X_1$, $X_2$, and $X_3$. Lone pairs of electrons from, e.g., the nitrogen atoms of the tridentate ligand, fill an unoccupied atomic orbital of the transition metal. This bonding scheme can also be described as σ-donation.

Representative, but not limited to, cobalt-containing compounds represented by formula (I) are shown below in Scheme 1:

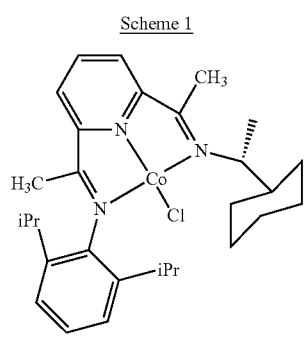

Scheme 1

-continued

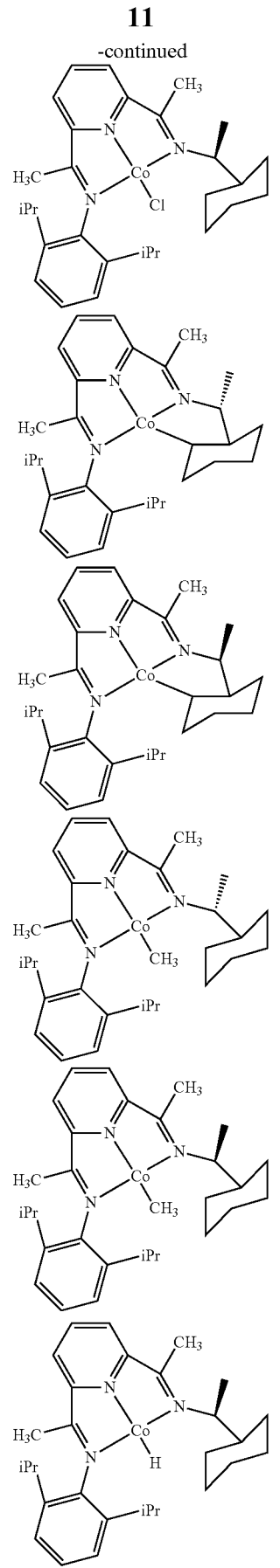

-continued

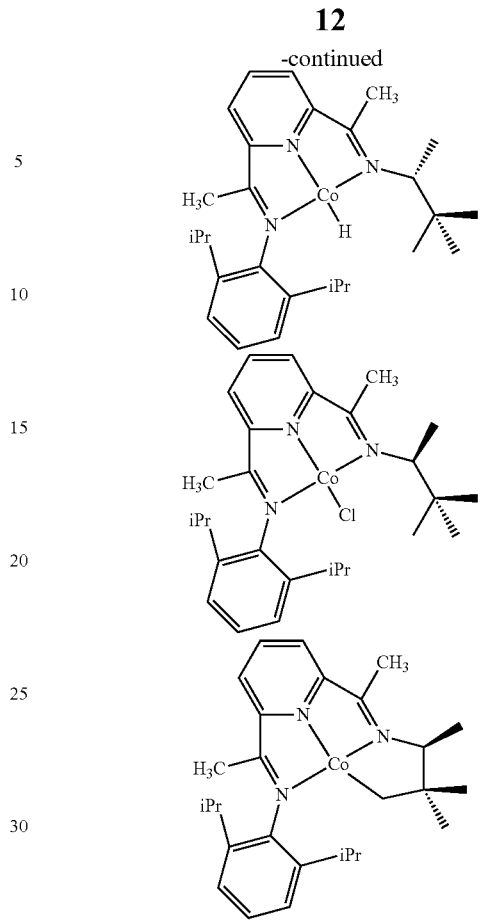

The present invention also includes methods of making the transition metal-containing complexes of formula (I). One method comprises reacting $X^3$ ligands with a transition metal source, e.g. $CoCl_2$, in the presence of a solvent, to produce five coordinate $\kappa^3\text{-}X^3\text{-}M\text{-}(R_1)(R_1')$ compounds. The temperature of this reaction is not particularly limited, but is preferably 20° C. to 100° C. (all intervening integers are included), further preferably about room temperature.

Next, the resulting $\kappa^3\text{-}X^3\text{-}M\text{-}(R_1)(R_1')$ compounds are reduced with one-electron reducing agents to remove the $R_1'$ group, thereby forming four coordinate $\kappa^3\text{-}X^3\text{-}M\text{-}R_1$ compounds. Alternatively, a $R_1'$ group can be replaced with a second $R_1$ group, so long as each $R_1$ group does not simultaneously represent a chloride ligand. This reducing reaction takes place at a temperature of, for example, −120° C. to 25° C. All intervening integers are included. The temperature can be changed during the reducing reaction, where, preferably, the temperature increases as the reducing reaction proceeds. For example, the temperature at the beginning of the reducing reaction is −120° C. and is increased to 25° C. over the course of the reaction. The reducing agent is not particularly limited, so long is it is capable of removing a $R_1'$ group. Examples of the reducing agent include, but are not limited to, sodium triethylborohydride, metals such as zinc and magnesium, and alkyl lithium compounds such methyl lithium, ethyl lithium, and n-butyl lithium. In the most preferred embodiments, the reducing agent comprises triethylborohydride in an amount sufficient to effect the reduction. The reducing agent is present in an amount of 0.01 to 5 equivalents, preferably 0.5 to 2 equivalents, more preferably from 0.5 to 1 equivalent, relative to the amount of the $\kappa^3\text{-}X^3\text{-}M\text{-}(R_1)(R_1')$ compounds. A second $R_1$ can be added to the four coordinate $\kappa^3\text{-}X^3\text{-}M\text{-}R_1$ compounds to produce transition metal-containing compounds within the scope of the present invention.

The four coordinate κ³-X³-M-(R₁) compounds where R₁ represents a halide ligand can be reacted with carbon-containing nucleophiles, such as, but not limited to, MeLi and MeMgBr, thereby replacing the halide with a carbon-containing group. Alternatively, 0.01 to 5 equivalents, preferably 0.5 to 2 equivalents, more preferably from 0.5 to 1 equivalent of the one electron reducing agent discussed above can be reacted with the κ³-X³-M-(R₁) compounds to form, it is believed, cyclometallated compounds. The resulting compounds are air and moisture sensitive. However, they can easily be handled under an inert (i.e. dinitrogen) atmosphere. Descriptions of particular syntheses for transition metal-containing compounds of the present invention can be found in the Monfette, S.; Turner, Z. R.; Semproni, S. P.; Chirik, P. J. *J. Am. Chem. Soc.* 2012, 134(10), 4561-4564 and the Supporting Information thereof. The entire contents thereof are herein incorporated by reference in their entireties.

The present invention also relates to catalysts that comprise the transition metal-containing compounds of the invention. The catalyst of the present invention comprises at least one of the transition metal-containing compounds represented by formula (I). In some embodiments of the present invention, the catalysts comprise additional components, such as solvents and supports, so long as the transition metal-containing compounds are present in the catalyst in an amount effective for catalyzing the hydrogenation of prochiral olefins. Preferably, the total amount of the transition metal-containing compounds represented by formula (I) present in the catalyst is from 0.5 to 10 mole %, relative to the total moles of the olefin.

In other embodiments of the invention, the present catalysts consist essentially of at least one at least one of the transition metal-containing compounds disclosed herein and components that do not materially affect the basic and novel characteristics of the catalysts disclosed herein, such as inert impurities that inevitably form during synthesis of these transition metal-containing compounds. In other embodiments of the present invention, the catalysts consist of the transition metal-containing compounds disclosed herein.

The solvent is not particularly limited, as long as the solvent is capable of dissolving the olefin and the transition metal-containing compounds represented by formula (I). An example of the solvent is benzene. The support is also not particularly limited, so long as these compounds are supported thereby. It can be, for example, silica or resin beads. In preferred embodiments, methylaluminoxane (MAO) is not present in the catalyst.

The transition metal-containing compounds represented by formula (I) are efficient in hydrogenating olefins, particularly prochiral olefins, which, once hydrogenated, have at least one chiral carbon atom in the molecule. The hydrogenation reactions can be carried out by charging a thick walled glass vessel with an olefin and a transition metal-containing compound represented by formula (I). A solvent is added to the glass vessel, and the atmosphere in the glass vessel is evacuated and replaced with hydrogen (H₂) at low temperatures, e.g. 80 K. The temperature of this reaction is not particularly limited, so long as it is sufficient to carry out the hydrogenation of the olefins. A preferred range for the reaction temperature is −20° C. to 50° C. All intervening integers are included. Most preferably, the hydrogenation reactions are carried out at about room temperature.

Additional applications include enantioselective preparation of active pharmaceutical ingredients, fragrances, agrochemicals, and biofuels. This is only one of the areas where the transition metal-containing compounds represented by formula (I) may be used industrially. The compounds are also competent for several other transformations and may be used for these processes as well. The transition metal-containing compounds represented by formula (I) and catalysts thereof are highly active, and as stated above, significantly less expensive to prepare.

The olefins of the catalyzed hydrogenation reactions are not particularly limited, but are preferably prochiral olefins. By way of example, (R)-propane-1,2-diyldibenzene and (S)-propane-1,2-diyldibenzene result from the hydrogenation of E-α-stilbene ((E)-prop-1-ene-1,2-diyldibenze), shown below, in the presence of transition metal-containing compounds represented by formula (I). The star indicates the chiral carbon atom:

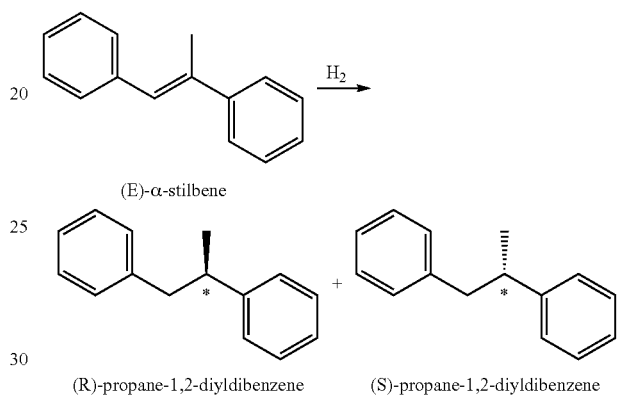

In preferred embodiments, the olefin comprises at least one of:

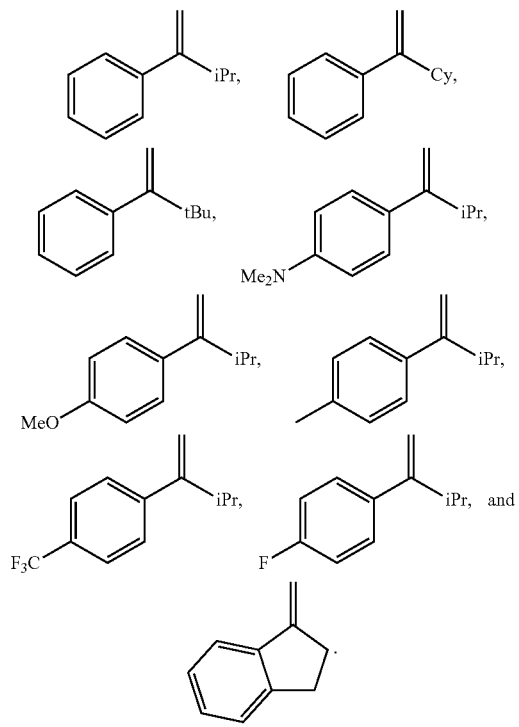

In other preferred embodiments, the olefin comprises α-limonene.

Another embodiment of the present invention relates to methods of making transition metal-containing catalysts for asymmetric catalysis, the methods comprising:

activating a compound represented by formula (V):

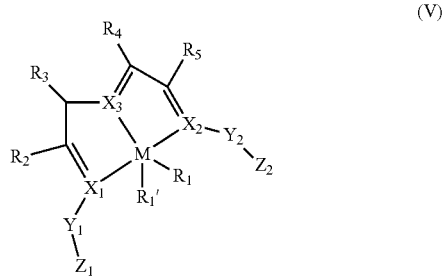

with a reducing agent to remove $R_1'$ or substituting $R_1'$ with a $R_1$ group, thereby forming a transition metal-containing compound according to formula (I), wherein M represents a transition metal atom selected from the group consisting of iron, cobalt, and nickel;

each of $X_1$, $X_2$, and $X_3$, individually, represents an element selected from the group consisting of nitrogen, phosphorus, and arsenic;

$Y_1$ represents a chemical bond between $X_1$ and $Z_1$ or a carbon-containing group that links $X_1$ and $Z_1$;

$Y_2$ represents a chemical bond between $X_2$ and $Z_2$ or a carbon-containing group that links $X_2$ and $Z_2$;

each of $Z_1$ and $Z_2$ represents a chiral group represented by formula (II) or a blocking group, with the proviso that at least one of $Z_1$ and $Z_2$ represents a chiral group represented by formula (II):

wherein each of $R_6$ and $R_7$, individually, represents $C_{1-20}$ alkyl group optionally having at least one heteroatom, a $C_{3-20}$ (hetero)cycloalkyl group, a $C_{5-30}$(hetero)aryl group, with the proviso that $R_6$ and $R_7$ do not simultaneously represent the same group, C* represents a nonracemic chiral carbon atom, and C* is bound to the $Y_1$ or $Y_2$ group or bound to $X_1$ or $X_2$ when $Y_1$ or $Y_2$ represents a chemical bond;

n represents an integer of 1 or 2;

each $R_1$, individually, represents a chemical bond to a carbon atom of $Y_1$, $Y_2$, $Z_1$ or $Z_2$, a hydrogen atom, a $C_{1-20}$ alkyl group optionally having at least one heteroatom, a $C_{3-20}$ (hetero)cycloalkyl group, a $C_{5-30}$(hetero)aryl group, or a halogen atom, with the proviso that when n represents an integer of 2, each $R_1$ does not, simultaneously, represent a halogen atom;

each of $R_2$ to $R_5$, individually, represents a $C_{1-20}$ alkyl group optionally having at least one heteroatom, a $C_{3-20}$ (hetero)cycloalkyl group, and an $C_{5-30}$(hetero)aryl group;

$R_2$ and $R_3$, together, can form a saturated, an unsaturated, or an aromatic ring having four, five, or six carbon atoms that is optionally interrupted with a heteroatom and is optionally substituted;

$R_3$ and $R_4$, together, can form a saturated, an unsaturated, or an aromatic ring having four, five, or six carbon atoms that is optionally interrupted with a heteroatom and is optionally substituted;

$R_4$ and $R_5$, together, can form a saturated, an unsaturated, or an aromatic ring having four, five, or six carbon atoms that is optionally interrupted with a heteroatom and is optionally substituted;

$R_2$ can form a saturated, an unsaturated, or an aromatic ring with a carbon atom of $Y_1$ or a carbon atom of $Z_1$ that has four, five, or six carbon atoms, is optionally interrupted with a heteroatom, and is optionally substituted; and $R_5$ can form a saturated, an unsaturated, or an aromatic ring with a carbon atom of $Y_2$ or a carbon atom of $Z_2$ that has four, five, or six carbon atoms, is optionally interrupted with a heteroatom, and is optionally substituted.

The preferred embodiments for $R_1$-$R_5$, $X_1$ to $X_3$, $Y_1$, $Y_2$, $Z_1$, and $Z_2$ in the compounds of formula (V) are the same as those defined above for the transition metal-containing compounds according to formula (I). All of these groups can be substituted with the substituting groups defined above in the transition metal-containing compounds represented by formula (I).

The reducing agent is not particularly limited, so long as it is capable of removing one $R_1'$. Examples of the reducing agent include, but are not limited to, sodium triethylborohydride, metals such as zinc and magnesium, and alkyl lithium compounds such methyl lithium, ethyl lithium, and n-butyl lithium. In the most preferred embodiments, the reducing agent comprises triethylborohydride in an amount sufficient to effect the reduction.

Transition metal-containing compounds represented by the following formula (Ia) are within the scope of formula (I):

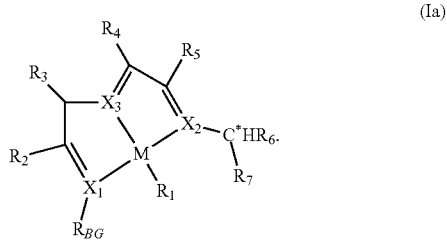

These compounds can exist in the form of salts. In the transition metal-containing compounds represented by formula (Ia), M represents a transition metal atom selected from the group consisting of iron, cobalt, and nickel;

each of $X_1$, $X_2$, and $X_3$, individually, represents an element selected from the group consisting of nitrogen, phosphorus, and arsenic;

$R_{BS}$ represents a blocking group;

$R_1$ represents a chemical bond to $R_6$ or $R_7$, a hydrogen atom, a $C_{1-20}$ alkyl group optionally having at least one heteroatom, a $C_{3-20}$ (hetero)cycloalkyl group, a $C_{5-30}$ (hetero)aryl group, or a halogen atom;

each of $R_2$ to $R_7$, individually, represents a $C_{1-20}$ alkyl group optionally having at least one heteroatom, a $C_{3-20}$ (hetero)cycloalkyl group, and an $C_{5-30}$(hetero)aryl group, with the proviso that $R_6$ and $R_7$ cannot represent the same group;

each of the couples of $R_2$ and $R_3$, of $R_3$ and $R_4$, and of $R_4$ and $R_5$ can form a saturated, an unsaturated, or an aromatic ring having four, five, or six carbon atoms that is optionally substituted; and C* represents a nonracemic chiral carbon atom.

Each of $X_1$, $X_2$, and $X_3$, individually, represents a nitrogen, phosphorus, or arsenic atom. Particularly preferred compounds are those compounds where each of $X_1$, $X_2$, and $X_3$ represents a nitrogen atom.

In the transition metal-containing compounds represented by formula (Ia), $R_1$ represents a chemical bond to $R_6$ or $R_7$, a hydrogen atom, a $C_{1-20}$ alkyl group, a $C_{3-20}$ (hetero)cycloalkyl group, a $C_{5-30}$(hetero)aryl group, or a halogen atom. Specific and non-limiting examples of the $C_{1-20}$ alkyl are the same as those defined above. It is possible for cyclometallated compounds to be formed when one of $R_6$ and $R_7$ are bound to the metal center M, where, in these compounds, $R_1$ represents a chemical bond between metal center M and $R_6$ or $R_7$.

Each of $R_2$ to $R_5$, individually, represents the same groups as defined above.

In the transition metal-containing compounds represented by formula (Ia), C* is a nonracemic chiral carbon atom, and, as a result, each of $R_6$ and $R_7$ cannot be the same group. Each of $R_6$ and $R_7$ are chemically bound to C*, and, individually, represents a $C_{1-20}$ alkyl group optionally having at least one heteroatom, a $C_{3-20}$ (hetero)cycloalkyl group, and an $C_{5-30}$ (hetero)aryl group, where these groups are defined the same as above. In one preferred embodiment, $R_6$ or $R_7$ represents a methyl group while the other of $R_6$ and $R_7$ represents a cyclohexyl group. In still another preferred embodiment, $R_6$ or $R_7$ represents a methyl group while the other of $R_6$ and $R_7$ represents a tert-butyl group. In yet another preferred embodiment, $R_6$ or $R_7$ represents a tert-butyl group while the other of $R_6$ and $R_7$ represents a methyl group.

In the transition metal-containing compounds represented by formula (Ia), the blocking group represented by $R_{BS}$ is defined as the same for the blocking group discussed above.

The present invention also relates to methods of hydrogenating and transforming olefins and alkynes in the presence of iron-containing compounds. These methods comprise reacting hydrogen with an olefin, an alkyne, or a mixture thereof, in the presence of at least one iron-containing compounds represented by formula (III):

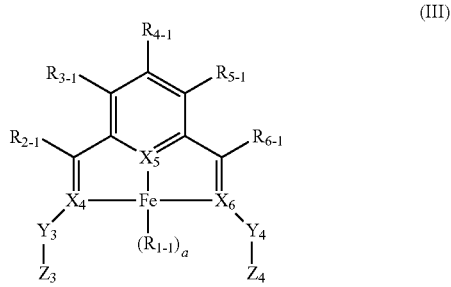

(III)

or a salt thereof,
wherein
each of $X_4$, $X_5$, and $X_6$, individually, represents an element selected from the group consisting of nitrogen, phosphorus, and arsenic;
$Y_3$ represents a chemical bond between $X_4$ and $Z_3$ or a carbon-containing group that links $X_4$ and $Z_3$;
$Y_4$ represents a chemical bond between $X_6$ and $Z_4$ or a carbon-containing group that links $X_6$ and $Z_4$;
each of $Z_3$ and $Z_4$, individually, represents a blocking group or a chiral group represented by formula (II);
a represents an integer of 1 or 2;
$R_{1-1}$, represents a chemical bond to a carbon atom of $Y_3$, $Y_4$, $Z_3$ or $Z_4$, a hydrogen atom, a $C_{1-20}$ alkyl group optionally having at least one heteroatom, a $C_{3-20}$ (hetero)cycloalkyl group, or a $C_{5-30}$(hetero)aryl group;
each of $R_{2-1}$ to $R_{6-1}$, individually, represents a hydrogen atom, a $C_{1-20}$ alkyl group optionally having at least one heteroatom, a $C_{3-20}$ (hetero)cycloalkyl group, or a $C_{5-30}$ (hetero)aryl group;
$R_{2-1}$ can form a (hetero)ring with a carbon atom from $Y_3$ or $Z_3$;
$R_{6-1}$ can form a (hetero)ring with a carbon atom from $Y_4$ or $Z_4$;
$R_{2-1}$ and $R_{3-1}$, together, can form a saturated, an unsaturated, or an aromatic ring having four, five, or six carbon atoms, is optionally interrupted with a heteroatom, and is optionally substituted; and
$R_{6-1}$ and $R_{6-1}$, together, can form a saturated, an unsaturated, or an aromatic ring having four, five, or six carbon atoms, is optionally interrupted with a heteroatom, and is optionally substituted.

The iron-containing compounds represented by formula (III) can be present in the form of a salt. In these compounds, each of $X_4$, $X_5$, and $X_6$, individually, represents an element selected from the group consisting of nitrogen, phosphorus, and arsenic. In preferred embodiments, at least one of $X_4$, $X_5$, and $X_6$ represents a nitrogen atom. In further preferred embodiments, at least two of $X_4$, $X_5$, and $X_6$ represent a nitrogen atom. In the most preferred embodiments, all three of $X_4$, $X_5$, and $X_6$ represent a nitrogen atom.

In the transition metal-containing compounds represented by formula (III), $Y_3$ represents a chemical bond between $X_4$ and $Z_3$ or a carbon-containing group that links $X_4$ and $Z_3$. The carbon-containing group is one that links or joins $X_4$ and $Z_3$ and has a chemical bond between each of $X_4$ and $Z_3$. This group is not particularly limited, so long as it does not remove the $Z_3$ group from the ligand sphere of the transition metal-containing compounds of the present invention, which could minimize the effect of the $Z_3$ group on the catalytic reactions. In preferred embodiments, $Y_3$ represents an alkylene group of one to six carbon atoms, which is represented by —$(CH_2)_m$—, where the symbol "-", in each occurrence, represents the chemical bond to each of $X_4$ and $Z_3$ and m is an integer of 1, 2, 3, 4, 5, or 6. The alkylene group can be substituted with at least one substituting group defined above. Preferably, the alkylene group is unsubstituted.

In the transition metal-containing compounds represented by formula (III), $Y_4$ represents a chemical bond between $X_6$ and $Z_4$ or a carbon-containing group that links $X_6$ and $Z_4$. The carbon-containing group is one that links or joins $X_6$ and $Z_4$ and has a chemical bond between each of $X_6$ and $Z_4$. This group is not particularly limited, so long as it does not remove the $Z_4$ group from the ligand sphere of the transition metal-containing compounds of the present invention, which could minimize the effect of the $Z_4$ group on the catalytic reactions. In preferred embodiments, $Y_4$ represents an alkylene group of one to six carbon atoms, which is represented by —$(CH_2)_m$—, where the symbol "-", in each occurrence, represents the chemical bond to each of $X_6$ and $Z_4$ and m is an integer of 1, 2, 3, 4, 5, or 6. The alkylene group can be substituted with at least one substituting group defined above. Preferably, the alkylene group is unsubstituted.

Each of $Z_3$ and $Z_4$ represents a blocking group. These groups are the same as those defined above for $Z_1$ and $Z_2$ in the transition metal-containing compounds represented by formula (I).

$R_{1-1}$ represents a chemical bond to a carbon atom of $Y_3$, $Y_4$, $Z_3$ and/or $Z_4$, a hydrogen atom, a $C_{1-20}$ alkyl group optionally having at least one heteroatom, a $C_{3-20}$ (hetero)cycloalkyl group, a $C_{5-30}$(hetero)aryl group, or a halogen atom. In preferred embodiments, $R_{1-1}$ represents a methyl group or a neopentyl group.

Each of $R_{2-1}$ to $R_{6-1}$, individually, represents a hydrogen atom, a $C_{1-20}$ alkyl group optionally having at least one heteroatom, a $C_{3-20}$ (hetero)cycloalkyl group, and an $C_{5-30}$(hetero)aryl group. These groups are the same as those defined above. In preferred embodiments, $R_{2-1}$ and $R_{3-1}$, together, form a saturated, an unsaturated, or an aromatic ring having four, five, or carbon atoms that is optionally interrupted with a heteroatom and is optionally substituted. Likewise, $R_{5-1}$ and $R_{6-1}$, together, can form a saturated, an unsaturated, or an aromatic ring having four, five, or six carbon atoms, which is optionally interrupted with a heteroatom, and which is optionally substituted with a substituting group defined above. In still further preferred embodiments, both $R_{2-1}$ and $R_{3-1}$ and $R_{5-1}$ and $R_{6-1}$ are joined to form saturated rings having four, five, or six carbon atoms. In the compounds of formula (III), at least one of $R_{3-1}$, $R_{4-1}$, and $R_{5-1}$ does not represent a hydrogen atom.

All of these groups can be substituted with the substituting groups defined above in the transition metal-containing compounds represented by formula (I).

Representative, but not limited to, iron-containing compounds of formula (III) for use in the methods of the present invention are shown below in Scheme 2:

Scheme 2

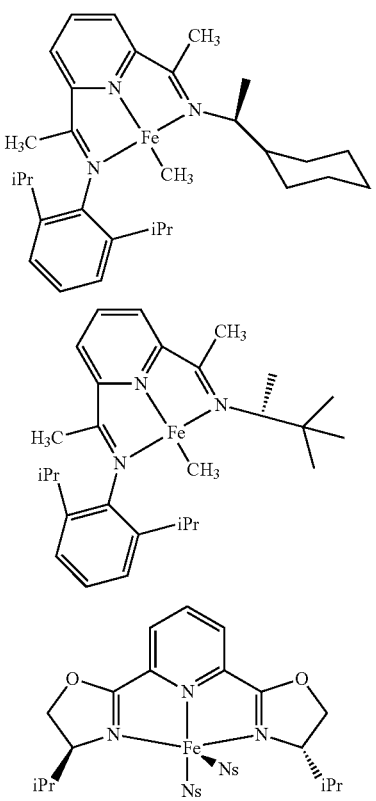

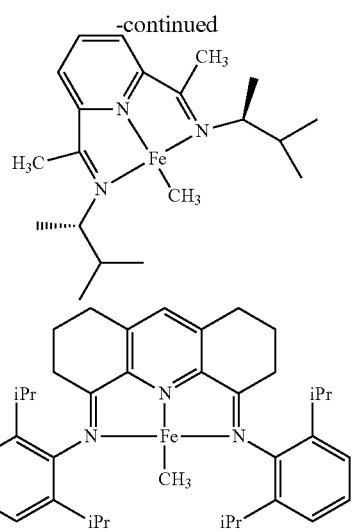

Many of these compounds are known and the syntheses for these compounds can be found in, e.g., Fernández, I.; Trovitch, R. J.; Lobkovsky, E.; Chink, P. J. *Organometallics* 2008, 27, 109-118.

In the methods of hydrogenating and transforming olefins and alkynes in the presence of iron-containing compounds represented by formula (III), the iron-containing compounds are present in an amount sufficient to catalyze the reactions. For example, the iron-containing compounds represented by formula (III) are present in an amount of 0.1 to 15 mole %, relative to the total moles of the substrate to be hydrogenated and/or transformed. The substrate comprises olefins and alkynes, which are not particularly limited, so long as they can be hydrogenated and/or transformed in the presence of these compounds. Preferred olefins are the same as those described above. Preferably, the alkyne comprises N-allyl-N-(but-2-yn-1-yl)-4-methylbenzenesulfonamide. The temperature for these reactions is not particularly limited, so long as it is sufficient for the reactions to proceed. Preferably, the range in reaction temperature is from −20° C. to 50° C. All intervening integers are included. Most preferably, the temperature for these reactions is about 45° C.

The methods can further comprise the following procedures. A first glass vessel is charged with at least one iron-containing compound represented by formula (III), which is dissolved in a solvent capable of dissolving the iron-containing compounds, e.g., benzene. A second glass vessel is charge with at least one of the substrates discussed above. The contents of the first and second glass vessels are transferred to a thick-walled glass vessel and chilled in, e.g., liquid nitrogen. The atmosphere in the thick-walled glass vessel is evacuated with a vacuum line attached to the thick-walled glass vessel. Hydrogen gas ($H_2$) is filled into the evacuated thick-walled glass vessel, which is carried out a low temperature, such as from 60 to 100 K, preferably from 70 to 90 K. All intervening integers are included. The temperature is increased to commence the reaction, where the reaction temperature is the same as discussed above. The product can be isolated and characterized by known methods, such as GC-FID and $^1$H-NMR.

The following non-limiting examples are intended to illustrate the present invention. Unless otherwise stated, the temperatures for the reactions are reported in degrees centigrade and all pressures are reported in atmospheres. The term "enantiomeric excess" or "ee" is defined as the concentration of the major enantiomer ([Major]) of the chiral product minus the concentration of the minor enantiomer ([Minor]) of the same product divided by the sum of the concentration of the major product and the concentration of the minor product, multiplied by one hundred percent:

$$ee = \frac{[\text{Major}] - [\text{Minor}]}{[\text{Major}] + [\text{Minor}]} \times 100\%$$

For those percentages that are reported with a greater-than symbol, this symbol means that the amount of the minor enantiomer was below the detection limit of the apparatus that measured the enantiomeric excess.

EXAMPLES

Example 1

Hydrogenation of Olefin A with Compound 1

In a drybox under a nitrogen atmosphere, 5 mole % of compound 1 and olefin A were placed in a glass vessel and dissolved in benzene. The glass vessel was taken out of the drybox and transferred to a high vacuum line. Following evacuation of the dinitrogen atmosphere, the glass vessel was loaded with four atmospheres of hydrogen ($H_2$), and the hydrogenation of olefin A was then carried out in the presence of compound 1 and at a temperature of 22° C. The reaction is shown below in Scheme 3. The conversion percentage and enantiomeric excess for the product are reported below in Table 1.

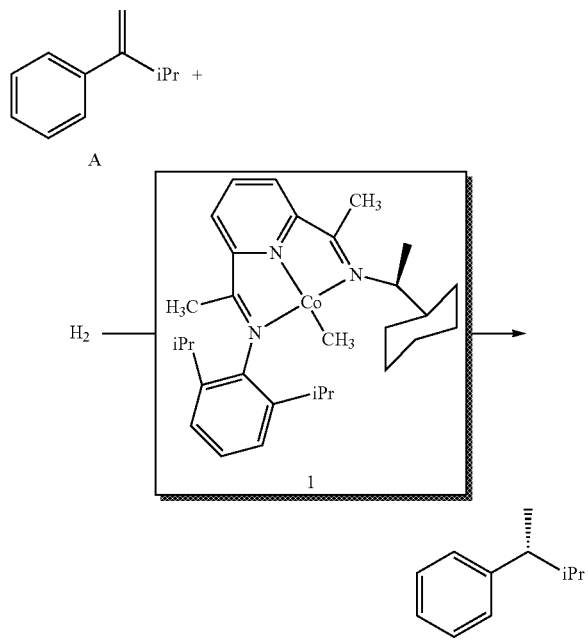

Examples 2-9

Hydrogenation of Olefin B to I with Compound 1

The same hydrogenation as Example 1 was carried out in these examples, with the exception of replacing olefin A with olefins B to I shown below in Scheme 4. The conversion percentages and enantiomeric excesses for the products are reported below in Table 1.

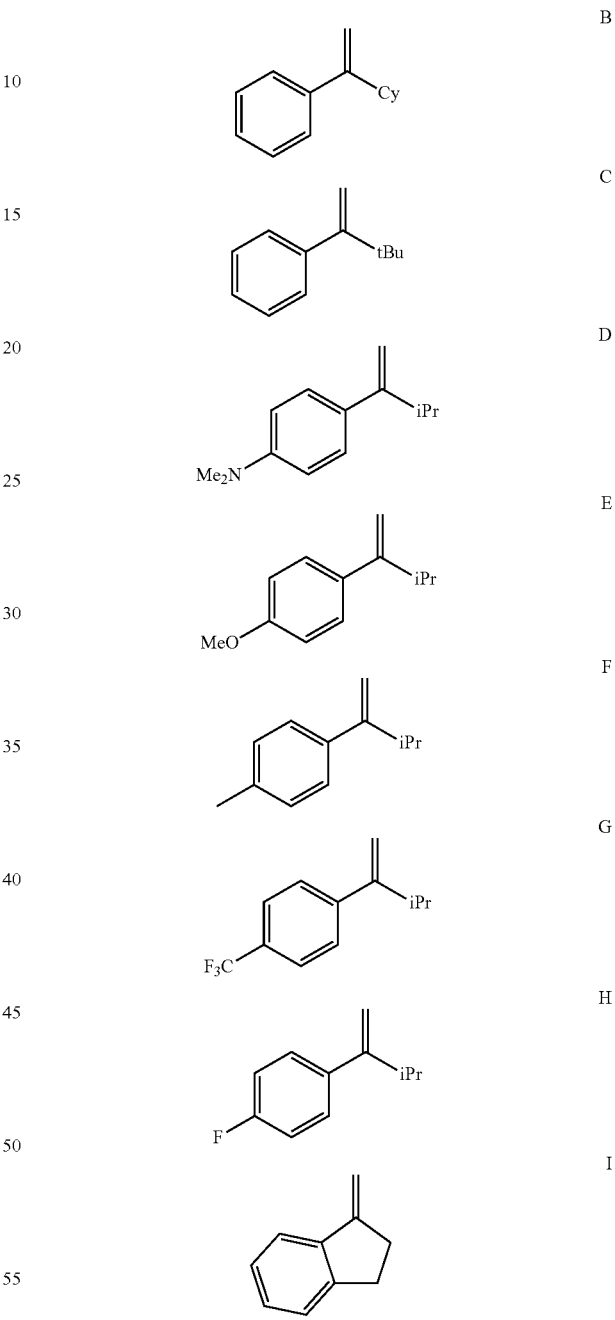

TABLE 1

| Example | Olefin | Conversion % | ee |
|---|---|---|---|
| 1 | A | 87% | 90% R |
| 2 | B | 70% | 80% R |
| 3 | C | 5% | >98% R |
| 4 | D | >98% | 96% R |
| 5 | E | >98% | 94% R |

TABLE 1-continued

| Example | Olefin | Conversion % | ee |
|---|---|---|---|
| 6 | F | >98% | 90% R |
| 7 | G | >98% | 78% R |
| 8 | H | >98% | 66% R |
| 9 | I | >99% | 39% S |

In Table 1, the conversion percentage refers to the percent of olefin converted to the alkane, relative to the entire amount of the olefin. This percentage and the enantiomeric excess values were determined with a gas chromatography (GC) flame ionization detector. GC analyses to determine the conversion percentages were performed using a Shimadzu GC-2010 gas chromatograph equipped with a Shimadzu AOC-20s autosampler, a Shimadzu SHRXI-5MS capillary column (15 m×250 µm) and a flame-ionization detector. UHP-grade helium was used as carrier gas with a flow rate of 1.12 mL/min. GC analyses to determine the enantiomeric excesses were performed using a Shimadzu GC-2010 gas chromatograph equipped with a Shimadzu AOC-20s autosampler and a Shimadzu BETA DEX 120 fused silica capillary column (30 m×0.25 mm×0.25 µm). Flow rates, temperatures, and other parameters can be adjusted by the skilled artisan for improved resolution of the residence times.

Example 10

Hydrogenation of Substrate I in the Presence of Compound 2

The same reaction of Example 9 was carried out, except that the olefin I was hydrogenated in the presence of compound 2. The conversion of olefin I in the presence of compound 2 was 44%. However, the enantiomeric excess in favor of the S enantiomer was 96%.

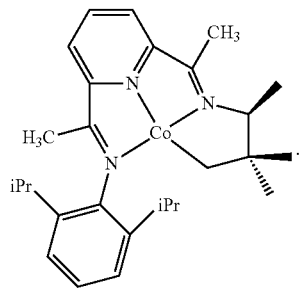

2

Example 11

Hydrogenation of α-Limonene in the Presence of Compound 3

In a drybox under a nitrogen atmosphere, 5 mole % of compound 3 and α-limonene were placed in a reaction vessel and dissolved in benzene. The reaction vessel was taken out of the drybox and transferred to a high vacuum line. Following evacuation of the dinitrogen atmosphere, the reaction vessel was loaded with four atmospheres of hydrogen ($H_2$), and the hydrogenation of α-limonene was then carried out for twenty four hours in the presence of compound 3 and at room temperature. The product obtained was (R)-4-isopropyl-1-methylcyclohex-1-ene at a conversion percentage of 70%.

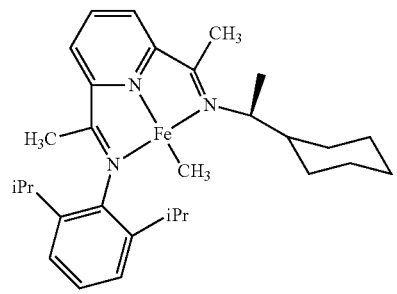

3

Example 12

Hydrogenation of Olefin A in the Presence of Compound 3

The same reaction of Example 11 was carried out, except that the concentration of compound 3 was increased to 10 mole % and α-limonene was replaced with olefin A. The conversion percentage was 17% and the enantiomeric excess in favor of the R enantiomer was 49%.

Example 13

Cyclization of N-allyl-N-(but-2-yn-1-yl)-4-methyl-benzenesulfonamide in the presence of compound 3

In a first glass vessel, compound 3 was dissolved in benzene. A second glass vessel was charged with the substrate, N-allyl-N-(but-2-yn-1-yl)-4-methylbenzenesulfonamide. The contents of the first and second glass vessels were mixed and transferred to a thick-walled glass vessel, which was submerged in liquid nitrogen and attached to a vacuum line. The atmosphere within the thick-walled glass vessel was evacuated and replaced with dihydrogen, and this process was carried out at 78 K. The solution in the thick-walled glass vessel was thawed to room temperature and the cyclization and hydrogenation of N-allyl-N-(but-2-yn-1-yl)-4-methyl-benzenesulfonamide was then carried out in the presence of compound 3 at 22° C. The obtained product was (Z)-3-ethylidene-4-methyl-1-tosylpyrrolidone. The conversion percentage was >98%, the yield of product was 88%, and the enantiomeric excess was ~0%.

Example 14

Cyclization of N-allyl-N-(but-2-yn-1-yl)-4-methyl-benzenesulfonamide in the presence of compound 4

The same reaction as Example 13 was carried out, except that compound 3 was replaced with compound 4. The obtained product was (Z)-3-ethylidene-4-methyl-1-tosylpyrrolidone. The conversion percentage was 50%, the yield of product was 47%, and the enantiomeric excess of the major enantiomer was between 20 and 30%.

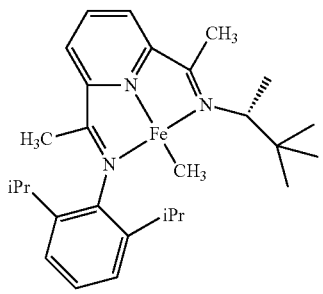

4

Example 15

Cyclization of N-allyl-N-(but-2-yn-1-yl)-4-methyl-benzenesulfonamide in the presence of compound 5

The same reaction as Example 13 was carried out, except that compound 3 was replaced with compound 5. The obtained product was (Z)-3-ethylidene-4-methyl-1-tosylpyrrolidone. The conversion percentage was >98%, and the yield of product was 68%.

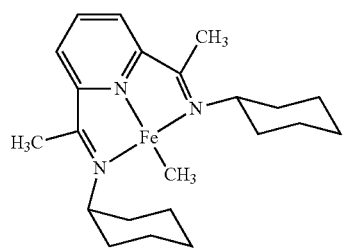

5

Example 16

Cyclization of N-allyl-N-(but-2-yn-1-yl)-4-methyl-benzenesulfonamide in the presence of compound 6

The same reaction as Example 13 was carried out, except that compound 3 was replaced with compound 6. The obtained product was (Z)-3-ethylidene-4-methyl-1-tosylpyrrolidone. The conversion percentage was >98%, the yield of product was 80%, and the enantiomeric excess of the major enantiomer was between 20 and 30%.

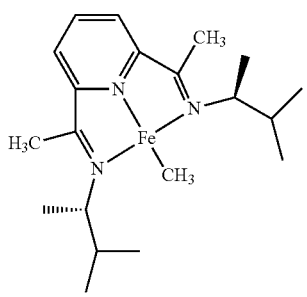

6

Example 17

Cyclization of N-allyl-N-(but-2-yn-1-yl)-4-methyl-benzenesulfonamide in the presence of compound 7

The same reaction as Example 13 was carried out, except that compound 3 was replaced with compound 7. The obtained product was (Z)-3-ethylidene-4-methyl-1-tosylpyrrolidone. The conversion percentage was >95% and the yield of product was 72%.

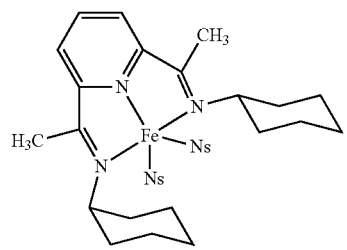

7

Example 18

Cyclization of N-allyl-N-(but-2-yn-1-yl)-4-methyl-benzenesulfonamide in the presence of compound 8

The same reaction as Example 14 was carried out, except that compound 3 was replaced with compound 8. The obtained product was (Z)-3-ethylidene-4-methyl-1-tosylpyrrolidone, and the conversion percentage was 12%.

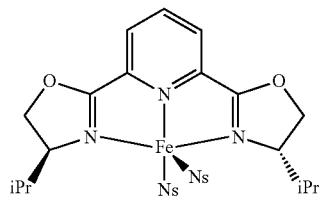

8

Example 19

Cyclization of N-allyl-N-(but-2-yn-1-yl)-4-methyl-benzenesulfonamide in the presence of compound 8

The same reaction as Example 18 was carried out, except that the time of hydrogenation was twenty four hours. The obtained product was (Z)-3-ethylidene-4-methyl-1-tosylpyrrolidone, and the conversion percentage was 44%.

Example 20

Hydrogenation of α-limonene in the presence of compound 9

In a drybox under a nitrogen atmosphere, 10 mole % of compound 9 and α-limonene were placed in a reaction vessel and dissolved in benzene. The glass vessel was taken out of the drybox and transferred to a high vacuum line. Following evacuation of the dinitrogen atmosphere, the glass vessel was loaded with four atmospheres of hydrogen ($H_2$), and the hydrogenation of α-limonene was then carried out for six hours in the presence of compound 9 and at 45° C. The product obtained was 1-isopropyl-4-methylcyclohexene at a conversion percentage of >98%.

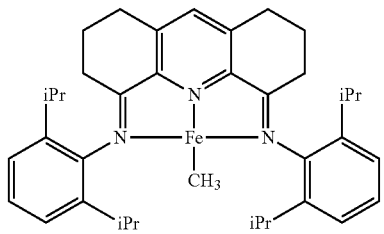

9

We claim:

1. A transition metal-containing compound, represented by formula (I):

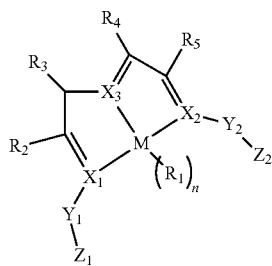

or a salt thereof,
wherein
M represents a transition metal atom selected from the group consisting of iron and cobalt;
each of $X_1$, $X_2$, and $X_3$ represents a nitrogen atom;
$Y_1$ represents a chemical bond between $X_1$ and $Z_1$ or a carbon-containing group that links $X_1$ and $Z_1$ represented by —$(CH_2)_m$—, where —, in each occurrence, represents the chemical bond to each of $X_1$ and $Z_1$ and m is an integer of 1, 2, 3, 4, 5, or 6;
$Y_2$ represents a chemical bond between $X_2$ and $Z_2$ or a carbon-containing group that links $X_2$ and $Z_2$ represented by —$(CH_2)_m$—, where—, in each occurrence, represents the chemical bond to each of $X_2$ and $Z_2$ and m is an integer of 1, 2, 3, 4, 5, or 6;
each of $Z_1$ and $Z_2$ represents a chiral group represented by formula (II) or a blocking group selected from the group consisting of an isopropyl group; a tert-butyl group; a neopentyl group; a cyclopropyl group; a cyclobutyl group; a cyclopentyl group; a cyclohexyl group optionally substituted with at least one methyl group, at least one ethyl group, at least one isopropyl group, at least one tert-butyl group, or a combination thereof; a phenyl group optionally substituted with at least one methyl group, at least one ethyl group, at least one isopropyl group, at least one a tert-butyl group, or a combination thereof; an adamantyl group; a trimethylsilyl group; a triethylsilyl group; a tripropylsilyl group; a tri-iso-propyl silyl group; a tri-tert-butyl group; and a neosilyl group, with the proviso that at least one of $Z_1$ and $Z_2$ represents a chiral group represented by formula (II):

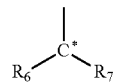

wherein each of $R_6$ and $R_7$, individually, represents $C_{1-20}$ alkyl group or a $C_{3-20}$ cycloalkyl group, with the proviso that $R_6$ and $R_7$ do not simultaneously represent the same group, C* represents a nonracemic chiral carbon atom, and C* is bound to the $Y_1$ or $Y_2$ group or bound to $X_1$ or $X_2$ when $Y_1$ or $Y_2$ represents a chemical bond;
n represents an integer of 1;
each $R_1$, individually, represents a chemical bond to a carbon atom of $Z_1$ or $Z_2$, a hydrogen atom, a $C_{1-20}$ alkyl group, or a halogen atom;
each of $R_2$ and $R_5$, individually, represents a $C_{1-20}$ alkyl;
$R_3$ and $R_4$, together, form an aromatic ring having five carbon atoms.

2. The transition metal-containing compound according to claim 1, wherein M represents an iron atom.

3. The transition metal-containing compound according to claim 1, wherein M represents a cobalt atom.

4. The transition metal-containing compound according to claim 1, wherein one of $Z_1$ and $Z_2$ represents a chiral group represented by formula (II), $R_6$ or $R_7$ represents a tert-butyl group or a cyclohexyl group and the other of $R_6$ and $R_7$ represents a methyl group.

5. The transition metal-containing compound according to claim 1, wherein one of $Z_1$ and $Z_2$ represents a chiral group represented by formula (II), $R_6$ or $R_7$ represents a tert-butyl group and the other of $R_6$ and $R_7$ represents a methyl group.

6. The transition metal-containing compound according to claim 1, wherein one of $Z_1$ and $Z_2$ represents a chiral group represented by formula (II), $R_6$ or $R_7$ represents a cyclohexyl group and the other of $R_6$ and $R_7$ represents a methyl group.

7. The transition metal-containing compound according to claim 1, wherein M represents a cobalt atom; one of $Z_1$ and $Z_2$ represents a chiral group represented by formula (II); $R_6$ or $R_7$ represents a tert-butyl group or a cyclohexyl group; and the other of $R_6$ and $R_7$ represents a methyl group.

8. The transition metal-containing compound according to claim 1, wherein M represents a cobalt atom; one of $Z_1$ and $Z_2$ represents a chiral group represented by formula (II); $R_6$ or $R_7$ represents a tert-butyl group; and the other of $R_6$ and $R_7$ represents a methyl group.

9. The transition metal-containing compound according to claim 1, wherein M represents a cobalt atom; one of $Z_1$ and $Z_2$ represents a chiral group represented by formula (II); $R_6$ or $R_7$ represents a cyclohexyl group; and the other of $R_6$ and $R_7$ represents a methyl group.

10. The transition metal-containing compound according to claim 1, wherein
each $R_1$, individually, represents a chemical bond to a carbon atom of $Z_1$ or $Z_2$; a hydrogen atom; a $C_{1-20}$ alkyl group selected from the group consisting of a methyl group, an ethyl group, a propyl group, and an isobutyl group; or a halogen atom; and
each of $R_2$ and $R_5$, individually, represents a $C_{1-20}$ alkyl group selected from the group consisting of a methyl group, an ethyl group, a propyl group, and an isobutyl group.

11. The transition metal-containing compound according to claim 1, which is:

12. The transition metal-containing compound according to claim 1, which is:

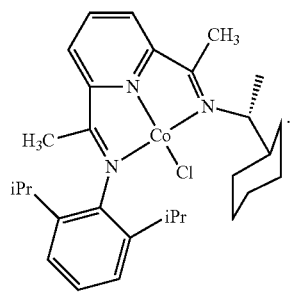

13. The transition metal-containing compound according to claim 1, which is:

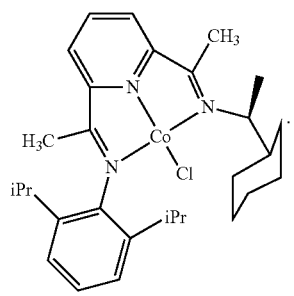

14. The transition metal-containing compound according to claim 1, which is:

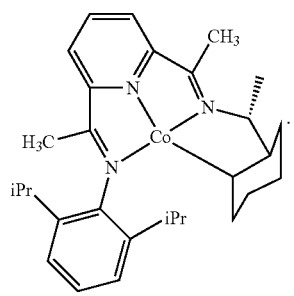

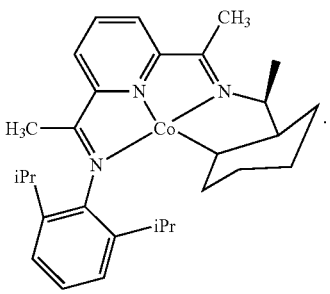

15. The transition metal-containing compound according to claim 1, which is:

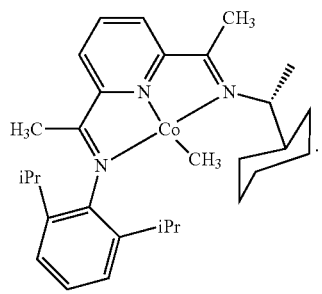

16. The transition metal-containing compound according to claim 1, which is:

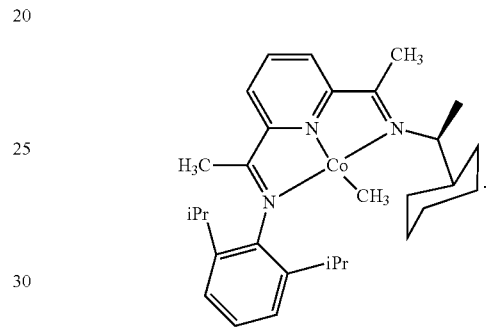

17. The transition metal-containing compound according to claim 1, which is:

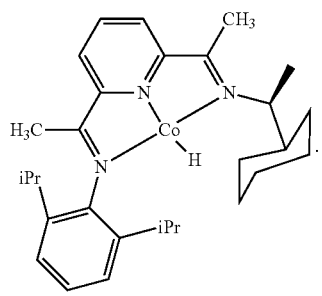

18. The transition metal-containing compound according to claim 1, which is:

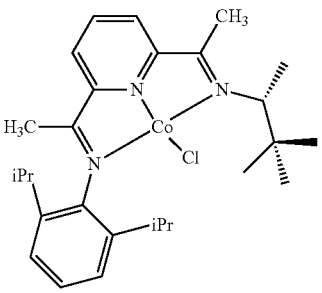

19. The transition metal-containing compound according to claim 1, which is:

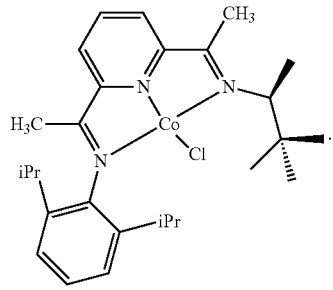

20. The transition metal-containing compound according to claim 1, which is:

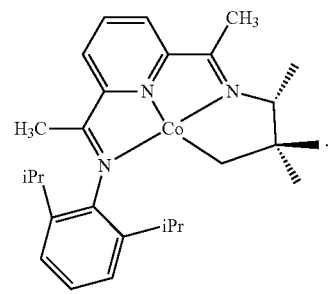

21. The transition metal-containing compound according to claim 1, which is:

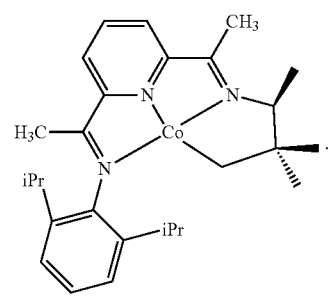

22. The transition metal-containing compound according to claim 1, which is:

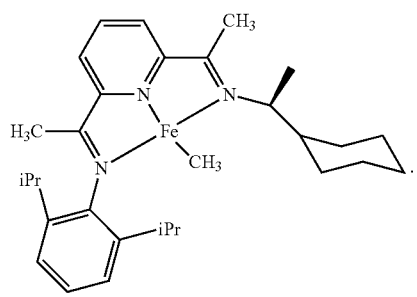

23. The transition metal-containing compound according to claim 1, which is:

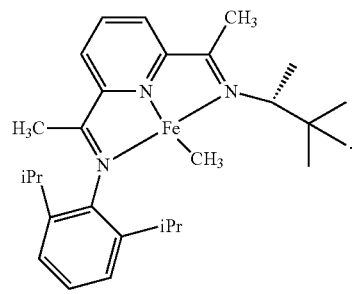

24. The transition metal-containing compound according to claim 1, which is:

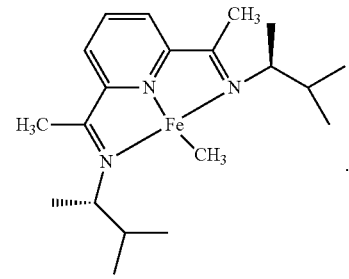

25. A catalyst comprising at least one transition metal-containing compound according to claim 1.

26. A method, comprising hydrogenating an olefin in the presence of a catalyst according to claim 25.

27. The transition metal-containing compound according to claim 1, wherein each of $Z_1$ and $Z_2$ represents a chiral group represented by formula (II) or a blocking that is a phenyl group optionally substituted with at least one methyl group, at least one ethyl group, at least one isopropyl group, at least one tent-butyl group, or a combination thereof.

28. A compound selected from the group consisting of

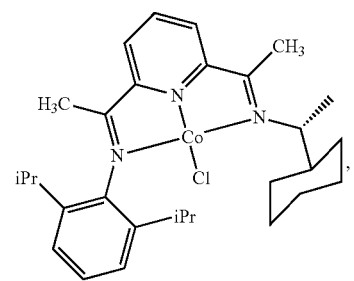

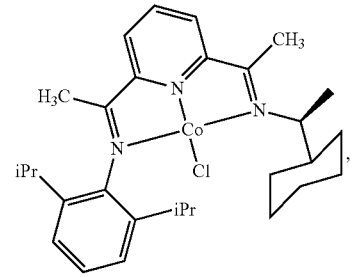

-continued
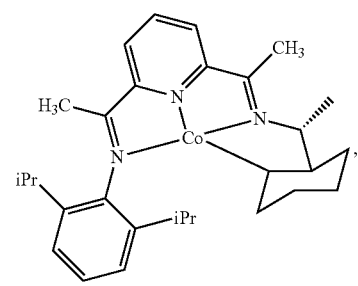
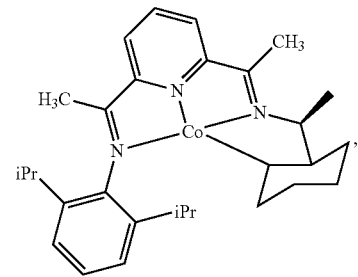
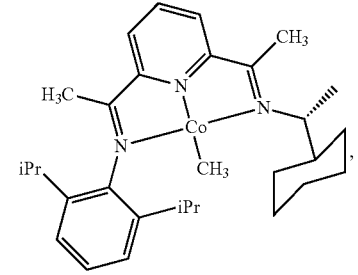
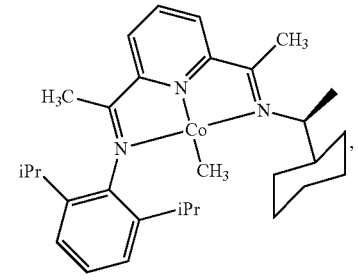
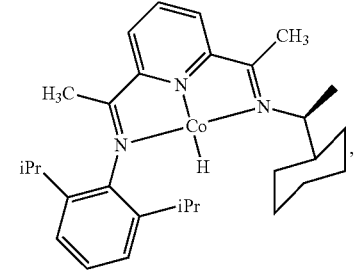
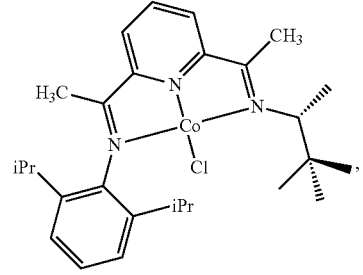
-continued
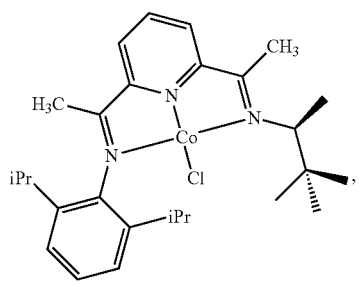
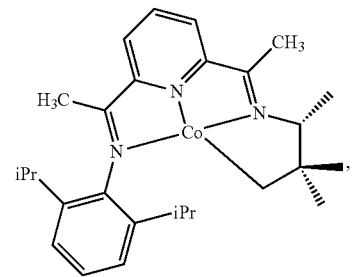
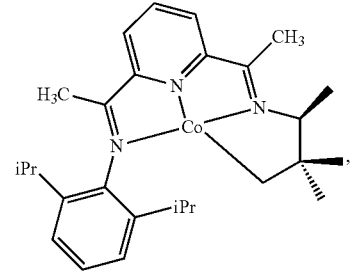
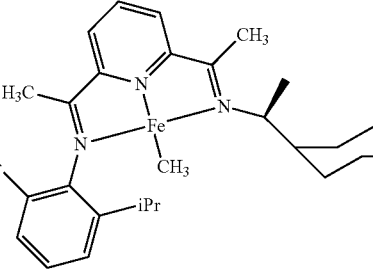
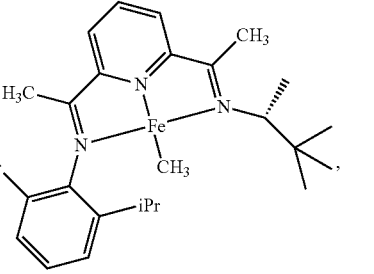, and
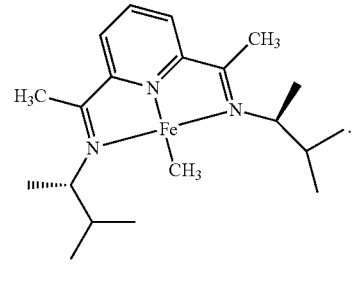

29. The transition metal-containing compound according to claim 1, wherein each $R_1$, individually, represents a chemical bond to a carbon atom of $Z_1$ or $Z_2$, a hydrogen atom, or a $C_{1-20}$ alkyl group.

30. The transition metal-containing compound according to claim 1, wherein each $R_1$, individually, represents a chemical bond to a carbon atom of $Z_1$ or $Z_2$ or a $C_{1-20}$ alkyl group.

\* \* \* \* \*